US00PP15667P2

(12) United States Plant Patent
Davidson

(10) Patent No.: US PP15,667 P2
(45) Date of Patent: Mar. 15, 2005

(54) HYBRID TEA ROSE PLANT NAMED 'HADMOO'

(50) Latin Name: *Rosa hybrida*
Varietal Denomination: Hadmoo

(76) Inventor: Harvey Daniel Davidson, 3 El Verano Rd., Orinda, CA (US) 94563

( * ) Notice: Subject to any disclaimer, the term of this patent is extended or adjusted under 35 U.S.C. 154(b) by 5 days.

(21) Appl. No.: 10/724,477

(22) Filed: Dec. 1, 2003

(51) Int. Cl.[7] ..... A01H 5/00
(52) U.S. Cl. ..... Plt./130
(58) Field of Search ..... Plt./130, 132, 137, Plt./138

*Primary Examiner*—Howard J. Locker

(57) ABSTRACT

A new and distinct rose cultivar of the Hybrid Tea class characterized by: having stems without prickles; large lavender flowers; flowers borne one to the stem; intense old damask fragrance; rapid repeat bloom; upright bushy plants of medium height.

1 Drawing Sheet

Botanical/commercial classification: *Rosa hybrida*/Hybrid Tea Rose Plant.

The cultivar name of this plant is designated as 'Hadmoo'. It is being marketed under the commercial name of 'Smooth Moonlight'.

The present invention relates to a new and distinctive cultivar of rose plant of the Hybrid Tea class, which was originated by my crossing 'Smooth Perfume' as the seed parent with 'Blue Boy' as the pollen parent.

Among the novel characteristics possessed by the new cultivar which distinguish it from:

(a) All other cultivars of which I am aware are:

(1) Prickles being absent from any stems.

(2) Large lavender flower with light pink to red petal edges.

(3) Single flower to the stem.

(4) Intense old damask fragrance.

(5) Very consistent free bloomer.

(b) Seed parent: Light lavender cluster flowers; no prickles. Pollen parent: Low growing; lavender flowers; few prickles.

Asexual reproduction of the new rose cultivar by budding onto the rootstock 'Dr. Huey', as performed at Wasco, Calif., shows that the aforementioned and all other distinctive characteristics come true to form and are established and transmitted through succeeding propagations.

The accompanying drawing shows typical specimens of the vegetative growth and flowers of the new cultivar in different stages of development and as depicted in color as nearly true as it is reasonably possible to make the same in a color illustration of this character.

The following is a detailed description of my new cultivar, with color terminology in accordance with The Royal Horticultural Society Colour Chart (R.H.S.C.C.). The terminology used in the color description herein refers to plate numbers such as 'Yellow Group 16A' found in Fan 1 of The Royal Horticultural Society Colour Chart.

Parentage:

*Seed parent.*—IRAR registered: 'Smooth Perfume'; Class Hybrid Tea; U.S. Plant Pat. No. 7,728.

*Pollen parent.*—'Blue Boy'; Class Hybrid Tea; Not patented.

The following observations are made of specimens grown outdoors in Orinda, Contra Costa County, Calif., in the month of October, 2003.

FLOWER

Blooming habit:

A. Bud:

(*1*) *Size.*—Sepals enclosed, 20–22 mm from base of sepals to top of bud.

(*2*) *Form.*—Ovoid.

(*3*) *Sepals.*—22 to 27 mm in length; 4 to 7 mm extension beyond bud; no serration shown on sepal edges. Generally 3 out of 5 sepals show appendages on each side, 2 to 4 mm length. Sepals show glandular development on edges. Heavy cotton matting on inner surface, fine matting on outer surface. Outside color: near to Red Group 38B with slight shadings of Greyed Red Group 181B; inside: Greyed Green Group 196A.

(*4*) *Peduncle.*—Length — 6 to 7 cm. Surface: smooth, some fine hairs, no glandular hairs, no prickles. Strength: firm. Color: near to Yellow Green 146C with shades of Greyed Orange Group 175B.

(*5*) *Receptacle.*—Shape: Oblong, 10–12 mm diameter; Color: same as peduncle.

(*6*) *Color.*—When sepals first divide, outside bud petals with shadings near to Red Purple Groups 63B–C and 62D.

B. Bloom:

(*1*) *Size.*—When open: 10–12 cm.

(*2*) *Borne.*—One flower per stem.

(*3*) *Form.*—Globular.

(*4*) *Petalage.*—Average — 36 to 40.

(*5*) *Color.*—Early open: outside petals with mixed shadings of Red Purple Groups 63B–C and 62D; inside petals similar to outside petals with shadings of Red Purple Group 74C and D on petal outer areas. Aging petals: near Purple Group 76C and D.

C. Petals:

(*1*) *Texture.*—Firm.

(*2*) *Appearance.*—Flexed; satiny.

(*3*) *Form.*—Early stages, symmetrically spaced. Aging: loses symmetry.

(*4*) *Arrangement.*—Regular.
(*5*) *Petaloids in center.*—Average 10 to 12.
(*6*) *Persistence.*—Holds well; petals drop cleanly at end of bloom.
(*7*) *Fragrance.*—Intense 'Old Damask'.
(*8*) *Lasting quality.*—On bush about 6–7 days; as cut flower about 4–6 days.

REPRODUCTIVE ORGANS

A. Stamen:
(*1*) *Arrangement.*—Regular around styles.
(*2*) *Number.*—Average: 140–150.
(*3*) *Length.*—Average: 5 to 10 mm from base.
(*4*) *Filaments.*—Color: Close to Yellow Orange Group 20D.
(*5*) *Anthers.*—Color: Yellow Orange Grp. 20D.
(*6*) *Pollen.*—Color: Yellow Orange Grp. 23B.

B. Pistil:
(*1*) *Styles.*—Length: 7–12 mm from center of ovary; number 120–125; color: near to Red Grp. 51B; sparsely coated with white hairs.
(*2*) *Stigma.*—Color — Close to Yellow Grp. 13D.
(*3*) *Ovary.*—Shape — oblong; 7–8 mm center cross section at sepal base.

C. Hips: Sets seed.
*Mature hip.*—2–2½ cm.
*Shape.*—Round.
*Color.*—Yellow Green 146C with shades near to Orange Grp. 28B.

PLANT

A. Form: Upright.
B. Growth: Height: average 1 m; Width: average 50 cm.
C. Stem length: Basal break to flower bud tip: average 90–100 cm.
D. Foliage: Compound of 3 to 5 leaflets on bloom stem; 5 to 7 leaflets on main canes.
(*1*) *Quantity.*—Stems well covered.
(*2*) *Color.*—New foliage: Upper side near to Yellow Green 147B with slight shading of Greyed Orange 176C on leaf edges; under side near to Yellow Green 147C. Old foliage: Upper side near to Yellow Green 147A; under side near to Yellow Green 146B.
(*3*) *Shape.*—Mature 5 leaflet: Length: stipule base to tip of leaflet — 10½–11½ cm. Center end leaflet: Oval and pointed. Length: 5–6 cm; Width: 4–4½ cm.
(*4*) *Texture.*—Firm, leathery, gloss finish.
(*5*) *Edge.*—Serration on outer edge: Average 5 to 6 points per 1 cm, with ½ to 1 mm peak.
(*6*) *Rachis.*—Very few glandular hairs on lower and upper side. No prickles on lower side.
(*7*) *Stipules.*—Length 15–16 mm; auricle to 3–4 mm. Edge of stipule to tip of auricle with many glandular hairs.

E. Resistance to disease: Powdery mildew: good. Rust and blackspot: Fair.
F. Wood:
*New wood.*—Color close to Yellow Green 146C; shadings near to Greyed Orange Group 176C; Bark — smooth.
*Old wood.*—Color close to Yellow Green 147B; Bark — smooth.
G. Prickles: None.
H. Winter hardiness: Average.

I claim:

1. A new and distinct rose cultivar of the hybrid tea class, characterized by prickles being absent from any stems, large lavender flowers borne singly, intense old damask fragrance, rapid repeat bloom, with the plant being upright, bushy and of medium height, substantially as herein shown and described.

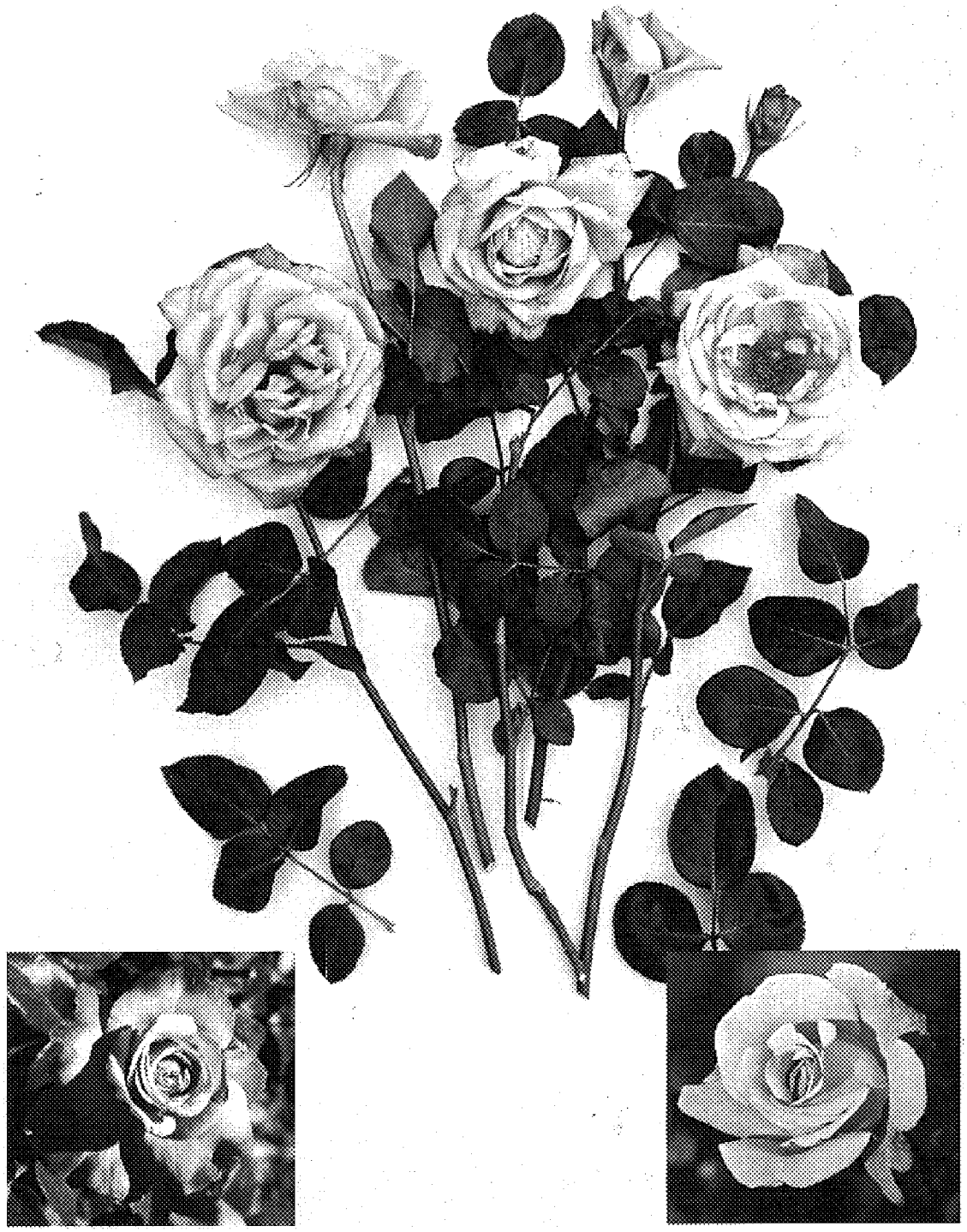

* * * * *